United States Patent
Li

(10) Patent No.: US 8,376,928 B2
(45) Date of Patent: *Feb. 19, 2013

(54) EXPANDABLE SURGICAL IMPLANTS AND METHODS OF USING THEM

(75) Inventor: Jamie Li, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 495 days.

This patent is subject to a terminal disclaimer.

(21) Appl. No.: 12/313,051

(22) Filed: Nov. 17, 2008

(65) Prior Publication Data

US 2009/0076318 A1    Mar. 19, 2009

Related U.S. Application Data

(63) Continuation of application No. 10/470,631, filed on Oct. 20, 2003, now Pat. No. 7,465,270, which is a continuation of application No. 09/972,377, filed on Oct. 5, 2001, now Pat. No. 6,666,817.

(51) Int. Cl.
    *A61F 2/02* (2006.01)
(52) U.S. Cl. .......................... 600/30; 606/151
(58) Field of Classification Search .............. 600/29–30, 600/37; 128/897–898; 606/151, 167, 196, 606/198, 205–209; 623/13.11
    See application file for complete search history.

(56) References Cited

U.S. PATENT DOCUMENTS

| | | | |
|---|---|---|---|
| 3,003,155 A | 10/1961 | Mielzynski et al. |
| 3,054,406 A | 9/1962 | Usher |
| 3,124,136 A | 3/1964 | Usher |
| 3,364,200 A | 1/1968 | Ashton |
| 3,580,313 A | 5/1971 | McKnight |
| 3,666,750 A | 5/1972 | Briskin et al. |
| 3,705,575 A | 12/1972 | Edwards |
| 4,347,847 A | 9/1982 | Usher |
| 4,452,245 A | 6/1984 | Usher |
| 4,633,873 A | 1/1987 | Dumican et al. |
| 4,655,221 A | 4/1987 | Devereux |
| 4,769,038 A | 9/1988 | Bendavid et al. |
| 4,838,884 A | 6/1989 | Dumican et al. |
| 4,905,692 A | 3/1990 | More |
| 4,911,165 A | 3/1990 | Lennard et al. |
| 4,973,300 A | 11/1990 | Wright |
| 4,986,831 A | 1/1991 | King et al. |
| 5,002,551 A | 3/1991 | Linsky et al. |
| 5,013,316 A | 5/1991 | Goble et al. |
| 5,026,398 A | 6/1991 | May et al. |
| 5,122,155 A | 6/1992 | Eberbach |
| 5,147,374 A | 9/1992 | Fernandez |
| 5,176,692 A | 1/1993 | Wilk et al. |
| 5,178,630 A | 1/1993 | Schmitt |

(Continued)

FOREIGN PATENT DOCUMENTS

| | | |
|---|---|---|
| EP | 0 599 772 | 6/1994 |
| EP | 0 643 945 | 3/1995 |

(Continued)

OTHER PUBLICATIONS

Wester's II New Riverside University Dictionary; 1984; p. 142.*

(Continued)

*Primary Examiner* — John Lacyk
(74) *Attorney, Agent, or Firm* — Bingham McCutchen LLP

(57) ABSTRACT

Disclosed herein are expandable surgical implants that may be expanded one or more times by directly or indirectly uncinching one or more expansion loops. Use of the expandable surgical implant permits a physician to expand, with minimal invasion, a surgical implant that was over-tensioned by a surgeon during implantation or became over-tensioned due to changes in the patient's anatomy.

18 Claims, 8 Drawing Sheets

U.S. PATENT DOCUMENTS

| | | | |
|---|---|---|---|
| 5,195,542 A | 3/1993 | Gazielly et al. | |
| 5,252,701 A | 10/1993 | Jarrett et al. | |
| 5,254,133 A | 10/1993 | Seid | |
| 5,292,328 A | 3/1994 | Hain et al. | |
| 5,354,292 A | 10/1994 | Braeuer et al. | |
| 5,362,294 A | 11/1994 | Seitzinger | |
| 5,366,460 A | 11/1994 | Eberbach | |
| 5,368,602 A | 11/1994 | de la Torre | |
| 5,425,740 A | 6/1995 | Hutchinson, Jr. | |
| 5,425,984 A | 6/1995 | Kennedy et al. | |
| 5,441,508 A | 8/1995 | Gazielly et al. | |
| 5,549,619 A | 8/1996 | Peters et al. | |
| 5,569,273 A | 10/1996 | Titone et al. | |
| 5,634,931 A | 6/1997 | Kugel | |
| 5,641,502 A | 6/1997 | Skalla et al. | |
| 5,645,849 A | 7/1997 | Pruss et al. | |
| 5,649,937 A | 7/1997 | Bito et al. | |
| 5,681,310 A | 10/1997 | Yuan et al. | |
| 5,707,647 A | 1/1998 | Dunn et al. | |
| 5,769,864 A | 6/1998 | Kugel | |
| 5,776,147 A | 7/1998 | Dolendo | |
| 5,813,975 A | 9/1998 | Valenti et al. | |
| 5,824,082 A | 10/1998 | Brown | |
| 5,836,314 A | 11/1998 | Benderev et al. | |
| 5,840,011 A | 11/1998 | Landgrebe et al. | |
| 5,899,909 A | 5/1999 | Claren et al. | |
| 5,916,225 A | 6/1999 | Kugel | |
| 5,919,232 A | 7/1999 | Chaffringeon et al. | |
| 5,922,026 A | 7/1999 | Chin | |
| 5,934,283 A | 8/1999 | Willem et al. | |
| 5,957,975 A | 9/1999 | Lafont et al. | |
| 6,039,686 A | 3/2000 | Kovac | |
| 6,042,534 A * | 3/2000 | Gellman et al. | 600/30 |
| 6,042,536 A | 3/2000 | Tihon et al. | |
| 6,053,935 A | 4/2000 | Brenneman et al. | |
| 6,068,591 A | 5/2000 | Bruckner et al. | |
| 6,090,116 A | 7/2000 | D'Aversa et al. | |
| 6,099,547 A | 8/2000 | Gellman et al. | |
| 6,102,921 A | 8/2000 | Zhu et al. | |
| 6,110,101 A | 8/2000 | Tihon et al. | |
| 6,221,005 B1 | 4/2001 | Bruckner et al. | |
| 6,319,264 B1 | 11/2001 | Tormala et al. | |
| 6,648,921 B2 | 11/2003 | Anderson et al. | |
| 6,652,450 B2 | 11/2003 | Neisz et al. | |
| 6,666,817 B2 | 12/2003 | Li | |
| 6,669,706 B2 | 12/2003 | Schmitt et al. | |
| 6,679,896 B2 | 1/2004 | Gellman et al. | |
| 6,736,823 B2 | 5/2004 | Darois et al. | |
| 6,755,781 B2 | 6/2004 | Gellman | |
| 7,465,270 B2 * | 12/2008 | Li | 600/30 |
| 2003/0114865 A1 | 6/2003 | Sater | |
| 2003/0191360 A1 | 10/2003 | Browning | |
| 2003/0225424 A1 | 12/2003 | Benderev | |
| 2004/0039246 A1 | 2/2004 | Gellman et al. | |
| 2004/0106847 A1 | 6/2004 | Benderev | |
| 2004/0111100 A1 | 6/2004 | Benderev et al. | |
| 2004/0144395 A1 | 7/2004 | Evans et al. | |
| 2004/0231678 A1 | 11/2004 | Fierro | |

FOREIGN PATENT DOCUMENTS

| | | |
|---|---|---|
| EP | 0643945 | 3/1995 |
| EP | 0 677 297 | 10/1995 |
| EP | 0 334 046 | 6/1997 |
| EP | 0 778 749 | 12/2000 |
| EP | 1 191 902 | 4/2002 |
| EP | 1 345 550 | 9/2003 |
| WO | WO-93/10715 | 6/1993 |
| WO | WO-96/06567 | 3/1996 |
| WO | WO-97/13465 | 4/1997 |
| WO | WO-97/30638 | 8/1997 |
| WO | WO-98/35632 | 8/1998 |
| WO | WO-00/74633 | 12/2000 |
| WO | WO-02/19945 | 3/2002 |
| WO | WO-02/062237 | 8/2002 |
| WO | WO-03/007847 | 1/2003 |

OTHER PUBLICATIONS

Araki, "The Loop-Loosening Procedure for Urination Difficulties after Stamey Suspension of the Vesical Neck," Urology 144:319-323 (1990).

Bayer, "A New Approach to Primary Strengthening of Colostomy with Marlex® Mesh to Prevent Paracolostomy Hernia," Surgery, Gynecology and Obstetrics 163:579-580 (1986).

Beck, "A 25-Year Experience with 519 Anterior Colporrhaphy Procedures, Obstetrics and Gynecology," 78:1011-1018 (1991).

Benderev, "A Modified Percutaneous Outpatient Bladder Neck Suspension System," J. Urology 152:2316-2320 (1994).

Benderev, "A New Endoscopic Bladder Neck Suspension for the Outpatient Treatment of Stress Urinary Incontinence," (video v-40) J. Urology 149:197A (1993).

Benderev, "Anchor Fixation and other Modifications of Endoscopic Bladder Neck Suspension," Urology 40:409-418 (1992).

Blaivas et al., "Pubovaginal Fascial Sling for the Treatment of Complicated Stress Urinary Incontinence," The Journal of Urology 145:1214-1218 (1991).

Cervigni et al., "Transvaginal Blader Neck Suspension: A Safer Method," Urology XXXVI (3):219-221 (1990).

Drutz et al. "Clinical and Urodynamic Re-evaluation of Combined Abdominovaginal Marlex Sling Operations for Recurrent Stress Urinary Incontinence," Intl. Urogynecol. J. 1:70-73 (1990).

Falconer, "Clinical Outcome and Changes in Connective Tissue Metabolism after Intravaginal Slingplasty in Stress Incontinent Women," Int. Urogynecol. J. 7:133-137 (1996).

Fianu et al., "Absorbable Polyglactin Mesh for Retropubic Sling Operations in Female Urinary Stress Incontinence," Gynecol. Obstet. Invest. 16:45-50 (1983).

Fiorelli et al., "Simplified Endoscopic Suspension for Stress Incontinence through Pervaginal Route," Arch. Esp. de Urol. 44(1):101-104 (1991).

Hom et al., "Pubovaginal Sling Using Polypropylene Mesh and Vesica Bone Anchors," Urology 51(5):708-713 (1998).

Horbach et al., "A Suburethral Sling Procedure with Polytetrafluoroethylene for the Treatment of Genuine Stress Incontinence in Patients with Low Urethral Closure Pressure," Obstetrics & Gynecology 71(4):648-652 (1988).

Iglesia et al., "The Use of Mesh in Gynecologic Surgery," Int. Urogynecol. J. 8:105-115 (1997).

Karram et al., "Transvaginal Needle Bladder Neck Suspension Procedures for Stress Urinary Incontinence: A Comprehensive Review," Obstetrics & Gynecology 73(5):906-914 (1989).

Keane et al., "Surgical Treatment and Complications of Urinary Incontinence," Current Opinion in Obstetrics and Gynecology 4:559-564 (1992).

Kersey, "The Guaze Hammock Sling Operation in the Treatment of Stress Incontinence," British J. Obstet. and Gynaecol. 90(10):945-949 (1983).

Kovac et al., "Pubic Bone Suburethral Stabilization Sling for Recurrent Urinary Incontinence," Obstetrics and Gynecology 89:624-627 (1997).

Leach et al., "Female Stress Urinary Incontinence Clinical Guidelines Panel Summary Report on Surgical Management of Female Stress Urinary Incontinence," The Journal of Urology 158:875-880 (1997).

Morgan et al., "The Marlex Sling Operation for the Treatment of Recurrent Stress Urinary Incontinence: A 16-Year Review," American J. of Obstet and Gynecol., 151(2):224-226 (1985).

Ou et al., "Laparoscopic Bladder Neck Suspension Using Hernia Mesh and Surgical Staples," J. Laparoendoscopic Surgery 3(6):563-566 (1993).

Petros, "The Intravaginal Slingplasty Operation, a Minimally Invasive Technique for Cure of Urinary Incontinence in the Female," Aust. NZ 1. Obstet. Gynaecol. 36(4):453-461 (1996).

Petros, "Ambulatory Surgery for Urinary Incontenance and Vaginal Prolapse," Med. J. Aust. 161:171-172 (1994).

Petros et al., "The Combined Intravaginal Sling and Tuck Operation. An Ambulatory Procedure for Cure of Stress and Urge Incontinence," Acta Obstet. Gynecol. Scand. 69(153):53-56 (1990).

Petros et al., "Non Stress Non Urge Female Urinary Incontinence—Diagnosis and Cure: A Preliminary Report," Acta Obstet. Gynecol. Scand. 69(153):69-70 (1990).

Petros et al., "The Development of the Intravaginal Slingplasty Procedure: IVS-II—(with bilateral "tucks")," Scand. J. Urol. Nephrol. Suppl. 153:61-67 (1993).

Petros et al., "Further Development of the Intravaginal Slingplasty Procedure: IVS-III—(with midline "tuck")," Scand. J. Urol. Nephrol. Suppl. 153:69-71 (1993).

Petros et al., "The Further Development of the Intravaginal Slingplasty Procedure: IVS-IV—(with "double-breasted" unattached vaginal flap repair and "free" vaginal tapes)," Scand. J. Urol. Nephrol. Suppl. 153:73-75 (1993).

Petros et al., "Further Development of the Intravaginal Slingplasty Procedure: IVS-V—(with "double-breasted" unattached vaginal flap repair and permenant sling)," Scand. J. Urol. Nephrol. Suppl., 153:77-79 (1993).

Petros et al., "The Intravaginal Slingplasty Procedure: IVS-VI—further development of the "double-breasted" vaginal flap repair attached flap," Scand. J. Urol. Nephrol. Suppl., 153:81-84 (1993).

Sarver et al., "Pubovaginal Slings: Past, Present and Future," Int. Urogynecol. J. 8:358-368 (1997).

Schaeffer et al., "Endoscopic Suspension fo teh Vesical Neck for Urinary Incontinence," Urology 23:484-494 (1984).

Stamey, "Endoscopic Suspension of the Vesical Neck," Surgery of Female Inconeinence, 115-132 (1986).

Stamey, "Endoscopic Suspension of the Vesical Neck for Urinary Incontinence," Surgery, Gynecology and Obstetrics 136:547-554 (1973).

Stanton, "Silastic Sling for Urethral Sphincter Incompetence in women," British Journal of Obsterics and Gynacecology, 92:747-750 (1985).

Ulmsten et al, "An Ambulatory Surgical Procedure Under Local Anesthesia for Treatment of Female Urinary Incontinence," Int. Urogynecol. J. 7:81-86 (1996).

Ulmsten et al., "Intravaginal Slingplasty (IVS): An Ambulatory Surgical Procedure for Treatment of Female Urinary Incontinence," Scand. J. Urol. Nephrol. 29:75-82 (1995).

Vasavada et al., "Incisionless Pubovaginal Fascial Sliing Using Transvaginal Bone Anchors for the Treatment of Stress Urinary Incontinence," www.duj. com/article/raz/raz.html, Jul. 24, 2001.

Webster, "Female Urinary Incontinence," Urologic Surgery, J.B. Lippinoctt Company: Philadelphia, 665-679 (1983).

* cited by examiner

EXPANDABLE SURGICAL IMPLANTS AND METHODS OF USING THEM

CROSS-REFERENCE TO RELATED APPLICATIONS

This application is a continuation of U.S. application Ser. No. 10/470,631 filed Oct. 20, 2003, which is a continuation of U.S. application Ser. No. 09/972,377, now U.S. Pat. No. 6,666,817, issued Dec. 23, 2003, the entire contents of which are incorporated herein by reference.

TECHNICAL FIELD

This invention generally relates to expandable surgical implants and methods of using such expandable surgical implants.

BACKGROUND INFORMATION

Numerous medical disease conditions that result from prolapse of internal organs and/or anatomical structures may be treated by providing support to the area of prolapse with a surgical implant such as a sling, a patch, or a mesh. Such implants are useful to treat, for example, stress urinary incontinence in female patients.

Various physiological conditions cause urinary incontinence in women. Stress urinary incontinence generally is caused by two conditions that occur independently or in combination, Intrinsic Sphincter Deficiency (ISD) and Bladderneck Hypermobility. ISD is a condition where the urethral sphincter valves fail to coapt properly. When functioning properly, the urethral sphincter muscles relax to enable the patient to void, and the sphincter muscles are otherwise constricted to retain urine. ISD may cause urine to leak out of the urethra during straining activities. Hypermobility is a condition where the pelvic floor is weakened or damaged causing the bladder neck and proximal urethra to descend in response to increases in intra-abdominal pressure. When intra-abdominal pressure increases (due, for example, to strain resulting from coughing), the hypermobility condition may cause urine leakage. Some women suffer from a combination of ISD and hypermobility.

The methods for treating stress urinary incontinence include placing an implant to provide support, elevation, or a "back stop" to the bladder neck and proximal urethra. Providing support to the bladder neck and proximal urethra maintains the urethra in the normal anatomical position, elevation places the urethra above the normal anatomical position, and the "back stop" prevents descent according to the so-called hammock theory.

One problem encountered following surgical intervention using an implant such as a sling or a patch to treat urinary incontinence is urinary retention resulting from excessive tension applied to the urethra. Overtensioning may also cause pressure necrosis and/or urethral erosion. One approach to alleviate these problems entails stretching the implant by inserting a catheter into the urethra and applying downward force. This procedure is imprecise and is contraindicated for patients with ISD as it may further damage the urethral sphincter. Another more invasive approach entails surgically removing the implant. Removal of such a surgical implant, which may require dissection, may cause irreparable damage to an already weakened or damaged pelvic floor. Accordingly, there is a need in the surgical arts for a surgical implant that may be expanded while positioned in the body. There is a further need for a precise and minimally invasive surgical method for expanding a surgical implant after it has been placed in the body.

SUMMARY OF THE INVENTION

It is an object of the invention to allow for expansion of a surgical implant while the implant is positioned in a body. Thus, the present invention provides for a surgical implant that may be expanded one or more times after being placed in the body, thereby providing a physician with the ability to loosen a surgical implant that was over-tensioned when placed by the surgeon and/or has become over-tensioned because of changes in the patient's anatomy. Thus, the expandable implant of the invention may be used, for example, in a suburethral sling procedure to treat female urinary incontinence by stabilizing the urethra, and later expanded if the patient suffers from urinary retention resulting from anatomical changes such as, for example, weight gain and/or pregnancy.

In one aspect, an expandable surgical implant having the features of the present invention may comprise a length of biocompatible material having at least one expansion loop positioned along the length of the biocompatible material and to one side of the center of the length (i.e., the central perpendicular axis of the implant).

In some embodiments, the expandable surgical implant may comprise an equal number of expansion loops that are positioned on either side of the central perpendicular axis; for example, the expandable surgical implant may comprise two, four, or six expansion loops positioned along the length of the biocompatible material and lateral to the central perpendicular axis. The expansion loops may each comprise at least one pair of control element attachment sites and at least one control element, such as a fastener, which is used to control the timing and degree of expansion. The pair of control element sites may be positioned on one side of the central perpendicular axis. The control elements may be attached to the control element sites and cinched so that the control element sites into are drawn into close proximity, thereby shortening the implant and facilitating its later expansion. In some preferred embodiments, a first control element site is positioned a distance ranging from 3-20 mm lateral to the central perpendicular axis of the length of biocompatible material and a second control element site is positioned a distance ranging from 3-12 mm further from the central perpendicular axis than the first control element. In particularly preferred embodiments, the second control element site is positioned a distance of about 5 mm further from the central perpendicular axis than the first control element site.

In some embodiments, the control element is a fastener such as a monofilament suture, a multifilament suture, an elongate length of biocompatible material, or a surgical staple. The control element attachment sites maybe reinforced to add resiliency to the implant at the expansion loop site or sites; for example, the control attachment site may be reinforced with an eyelet or an additional layer of biocompatible material.

In some embodiments, the control element is radio-opaque to facilitate indirect visualization of the control element site by a physician using the expandable surgical implant. When the control element is radio-opaque, it may be visualized using an instrument such as a fluoroscope. To facilitate direct visualization, the control element may a different color than the biocompatible material. Such direct and/or indirect visualization is particularly useful when expanding the surgical implant of the invention following implantation.

The control element may comprise bioabsorbable material so that it dissolves without physician intervention to thereby permit the implant to expand at the predetermined time. In alternative embodiments the control element is adapted to decompose upon application of external stimuli, thus permitting a physician to expand the implant at any desired time. For example, the control element may be adapted to decompose upon exposure to a localized low energy source or a chemical agent. The localized low energy may be in the form of, for example, ultrasonic waves, radio waves, microwaves, and ultraviolet radiation. The expandable surgical implant may comprise multiple expansion loops associated with control elements adapted to decompose upon the application of separate external stimuli. In such embodiments, the expandable surgical implant may be expanded multiple times by applying multiple stimuli (e.g., different forms or intensities of energy) that decompose different control elements. For example, the expandable surgical implant may be expanded a first time by applying one stimulus that decomposes a first control element and, possibly, a second control element, and subsequently expanded further by applying a separate stimulus that decomposes a third control element and, possibly, a fourth control element.

In some embodiments, the expandable loop comprises multiple layers of biocompatible material of unequal length. The layers of biocompatible material may, for example, be stacked in increasing length. In preferred embodiments, each layer of biocompatible material is about 2 mm to about 10 mm shorter than the adjacent longer layer in the stack of biocompatible material. In particularly preferred embodiments, the each layer of biocompatible material is about 5 mm shorter than the adjacent longer layer of biocompatible material in the stack. Furthermore, the layers of biocompatible material are preferably positioned a distance ranging from 3-20 mm lateral to the central perpendicular axis. In particularly preferred embodiments, the layers of biocompatible material are 6 mm lateral to the central perpendicular axis.

In some embodiments, the expandable surgical implant comprises a length of biocompatible material that is synthetic, such as, for example, nylon, polyethylene, polyester, polypropylene, one or more fluoropolymers such as polyfluoroethylene and/or combinations thereof. In alternative embodiments, the length of biocompatible material comprises natural material. In further alternative embodiments, the length of biocompatible material comprises a combination of natural and synthetic material. In one particular embodiment, the expandable surgical implant comprises a length of biocompatible material having a central portion comprising natural material and the first end portion and second end portion comprise synthetic material.

The expandable surgical implant may comprise a visual indicator located along at least a portion of the central perpendicular axis. The visual indicator may comprise, for example, a surgical dye applied along the central perpendicular axis. The visual indicator may alternatively comprise a radio-opaque material woven into the biocompatible material along the central perpendicular axis.

In some embodiments, the length of biocompatible material is elongate (e.g., rectangular) in shape. For example, the length of biocompatible material may be about 44 cm to 47 cm long with all expansion loops cinched.

In another aspect, the present invention is directed to methods of treating urinary incontinence. An expandable surgical device comprising at least one expansion loop is implanted into a patient to support the urethra. The device is then expanded to reduce the amount of tension applied to the urethra. Thus, the invention provides a surgeon with the ability to loosen a surgical implant (e.g., to ameliorate urinary retention caused by an excessively taut implant or to accommodate a pregnancy).

In some embodiments, an expandable surgical device is implanted into a patient and subsequently loosened. The implanted device may comprise a biocompatible material having a length, a central perpendicular axis normal to the length and located substantially equidistant from the ends of the device, and at least one expansion loop into a patient. The expansion loop(s) are positioned along the length of the biocompatible material lateral to the central perpendicular axis.

In some embodiments, the expandable surgical device is implanted beneath the bladder neck; for example, the expandable surgical device may be implanted beneath the first third or the central third of the urethra. The device may be affixed to an anatomical structure selected by the surgeon according to the particular anatomy of the patient. The device may be attached, for example, to fascia, bone, ligament, and/or muscle. The method of invention may further comprise aligning the central portion of the device beneath the urethra using a visual indicator located along at least a portion of the central perpendicular axis. Expansion may be accomplished by severing the shorter of at least two layers of material of unequal length incorporated into the biocompatible material. Alternatively, expansion may be accomplished by severing a control element (e.g., a fastener) which holds two laterally distant portions of the implant in close proximity (i.e., creates a loop).

Thus, in other embodiments, expansion is accomplished by uncinching the control element, which holds in close proximity a pair of control element sites that are located on the on one side of the central axis. The uncinching may be accomplished by severing the control element. The control element may be severed using mechanical means such as, for example, a scalpel. Alternatively, the uncinching may be accomplished by applying an external stimulus to cause the control element to decompose. For example, localized low energy (e.g., ultrasonic waves, radio waves, microwaves, and/or ultraviolet radiation) may be applied to the control element to stimulate decomposition and severance of the control element, which in turn permits the expandable surgical implant to expand. In some approaches the control element is radio-opaque and may be visualized without incision by, for example, fluoroscopy. The foregoing methods that, preferably, do not require an incision to sever the control element facilitate adjustment of an expandable surgical implant with minimal or no surgical invasion.

In some embodiments, the expandable surgical implant may be expanded multiple times by uncinching multiple expandable loops. In one particular embodiment, the expandable surgical implant is expanded multiple times by the application of a combination of different external stimuli which decompose different control elements causing the expansion loops attached by the different control elements to become uncinched. This aspect of the method of the invention affords the physician great flexibility in adjusting expandable surgical implants; the physician may, for example, select one of several expansion loops to expand according to position or size by applying the external stimulus specific to decompose a specific control element.

These and other features, aspects, and advantages of the present invention will become better understood with reference to the following description and appended drawings.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

Figure 1:
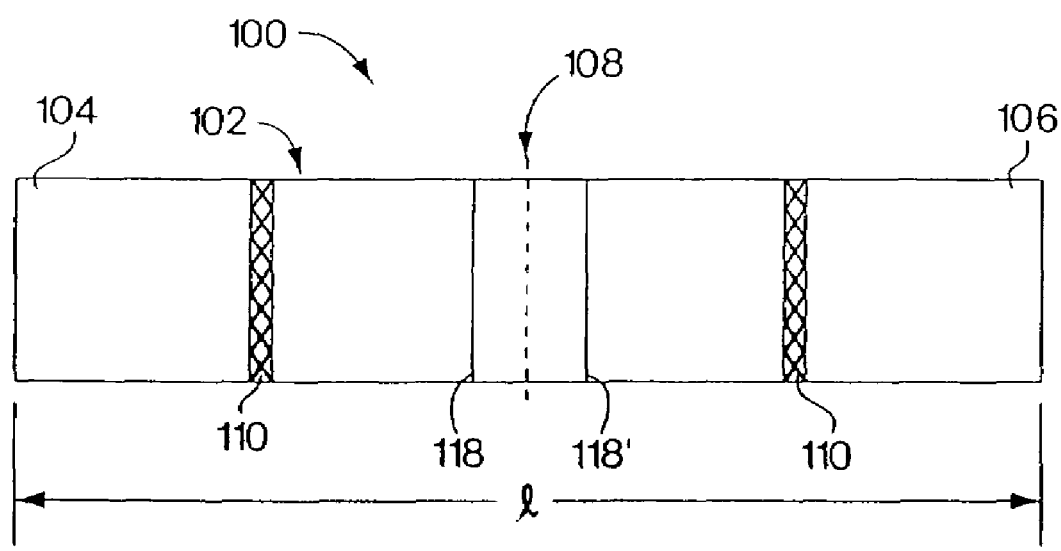
FIG. 1 is a plan view of one disclosed embodiment of an expandable implant of the invention.

Referring to FIG. 1 an expandable surgical implant 100 of the present invention can be made of a length, "1, of biocompatible material 102 which includes a first end 104 and a second end 106 positioned opposite to the first end 104, and a central perpendicular axis 108 located midway between the ends 104, 106. The expandable surgical implant 100 of the invention also comprises at least one expansion loop 110. In preferred embodiments, an equal number of expansion loops are preferably positioned on either side of the central perpendicular axis 108 (as shown in FIG. 1). In some embodiments the expandable surgical implant 100 may further comprise a visual indicator 118 located along the central perpendicular axis 108. The visual indicator shown in FIG. 1 comprises a pair of lines 118 and 118' positioned on either side of the central perpendicular axis 108. The expandable surgical implant 100 may comprise multiple (e.g., one to ten) expansion loops 110. In preferred embodiments, the expandable surgical implant 100 comprises two, four, or six expansion loops 110.

Figure 2A:
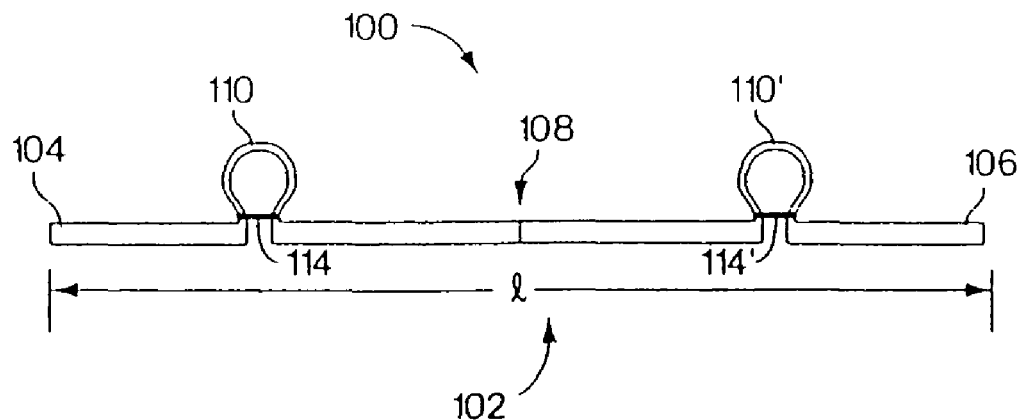
FIG. 2A is a side view of the cinched-loop embodiment of the expandable implant of the invention.
Figure 2B:
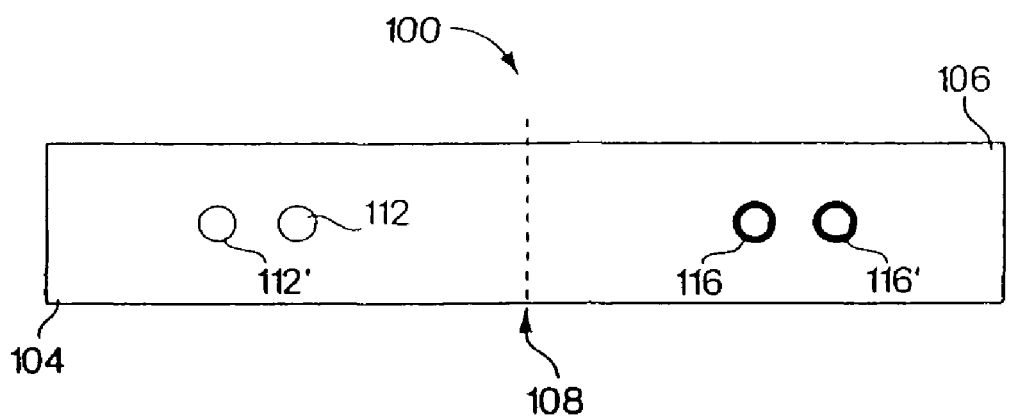
FIG. 2B is a plan view of the cinched-loop embodiment of the expandable implant of the invention.
Figure 2C:
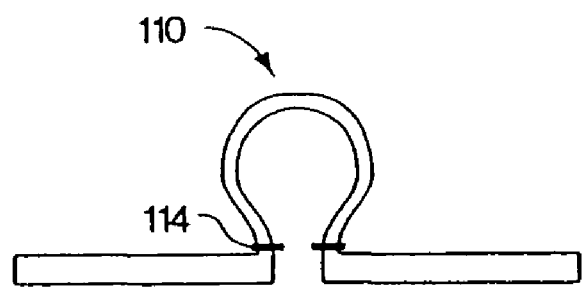
FIG. 2C is a side view of a cinched-loop showing the control element severed to expand the length of the implant.

FIGS. 2A, 2B, and 2C depict some of the features of the "cinched-loop" embodiment of the expandable surgical implant 100. In this embodiment, the expansion loops 110 and 110' comprise at least one pair of control element attachment sites 112 and 112' positioned away from the central portion of the implant. The control element attachment sites 112 and 112' may be reinforced, for example with an eyelet 116 and 116' (as shown in FIG. 2B) or an additional piece of biocompatible material.

The expandable surgical implant may be specifically configured as a sling for treating female urinary stress incontinence. In such embodiments, a first control element attachment site 112 is preferably positioned a distance ranging from 3 to 20 mm lateral to the central perpendicular axis 108 of the length of biocompatible material and a second control element attachment site 112' is preferably positioned a distance ranging from 3 to 12 mm further from the central perpendicular axis 108 than the first control element attachment site 112. In particularly preferred embodiments, the second control element attachment site 112' is positioned a distance of about 5 mm further from the central perpendicular axis 108 than the first control element attachment site 112. The pair of control element sites is preferably located on one side of the central perpendicular axis 108 so that the expansion loop they form is also lateral to the central axis 108, a configuration that will minimize damage to the suburethral tissue (including tissue that may have grown into the sling) which may occur when the expansion loops is expanded. As shown in FIG. 2B, the implant 100 may have a second pair of control element attachment sites located on the opposite side of the central perpendicular axis 108.

FIG. 2A shows a pair of expansion loops 110, 110' cinched with a pair of control elements 114, 114'. In the cinched-loop embodiments, expansion is accomplished by uncinching the control element 114, which holds the corresponding pair of control element sites 112, 112' in close proximity. FIG. 2C illustrates a cinched loop in which the control element 114 has been severed.

Uncinching the control element 114 may be accomplished in several different ways. The expansion loop may be uncinched, for example, by mechanically severing the control element 114, bioabsorbing the control element 114, or decomposing the control element 114 by the application of an external stimulus. Thus, the control element 114 may be severed, for example, by using mechanical means such as a scalpel, or it may be broken down by the body during a predetermined time interval, or decomposed by localized low energy. Forms of low energy that may be used to decompose a control element may include, without limitation, ultrasonic waves, radio waves, microwaves, and ultraviolet radiation.

In some embodiments, the control element 114 is a fastener such as a monofilament suture, a multifilament suture, a ribbon of biocompatible material, or a surgical staple. The control element attachment sites 112 and 112' may be reinforced to add resiliency to the expandable surgical implant 100 at the expansion loop 110 site or sites. Thus, in some embodiments, the control element attachment sites 116, 116' may be reinforced with an eyelet (shown in FIG. 2B) or an additional layer of biocompatible material. The eyelet may be composed of any), resilient biocompatible material such as surgical metals and/or polymers.

In some embodiments, the control element 114 may comprise radio-opaque materials (for example, metals such as stainless steel, superalloys, nitinol, and/or titanium) that may be indirectly visualized (i.e., without making an incision and/or dissecting to expose the control element 114). Such radio-opaque control elements may be visualized, for example, by fluoroscopy.

In alternative embodiments, the control element 114 may be comprised entirely of materials with relatively low radiodensities that may not be indirectly visualizable. In such embodiments, the control element 100 may be directly visualized following incision and/or dissection. To facilitate direct visualization, the control element 114 may be a different color than the length of biocompatible material 102. Direct and/or indirect visualization of the control element 114 is particularly useful when the surgical implant is expanded after implantation.

Figure 3A:
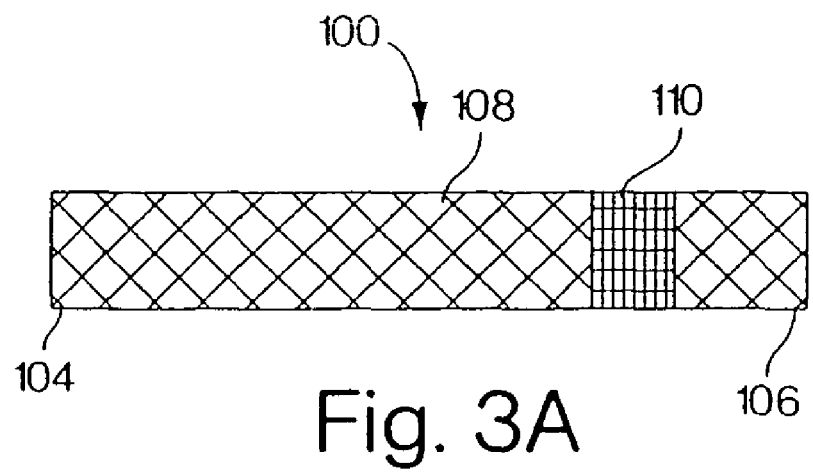
FIG. 3A is a plan view of the stacked-layers embodiment expandable implant.
Figure 3B:
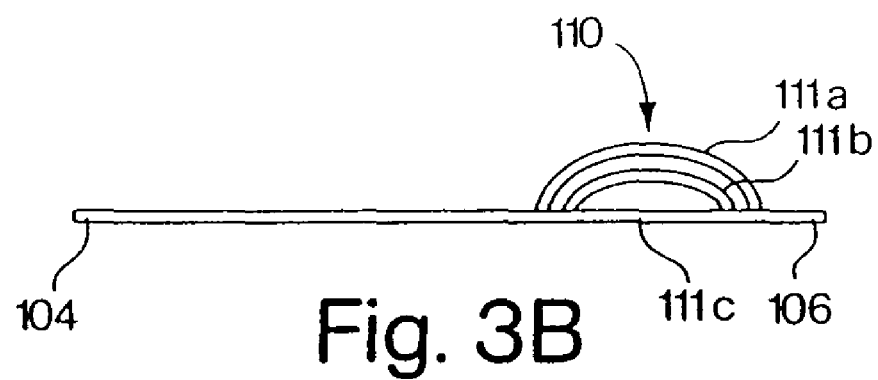
FIG. 3B is a side view of the stacked-layers embodiment of the expandable implant of the invention, which shows three stacked layers.
Figure 3C:
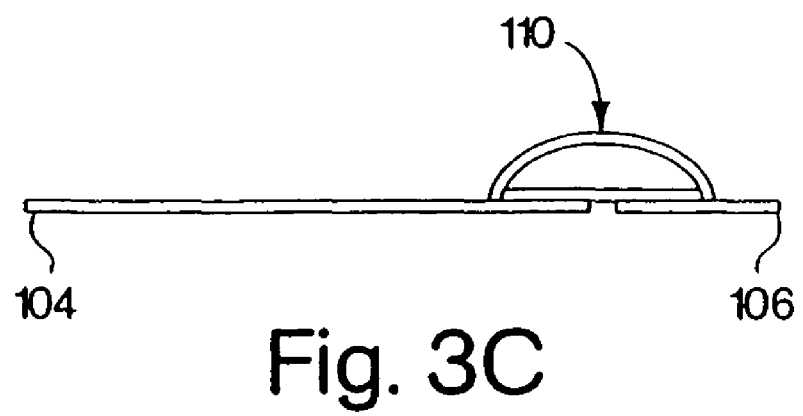
FIG. 3C is an elevation of the stacked-layers embodiment of the expandable implant of the invention showing one layer severed to expand the length of the implant.

FIGS. 3A, 3B, and 3C depict the "stacked-layers" embodiment of the expandable surgical implant 100. In the stacked-layers embodiment, the expandable loop comprises multiple layers of biocompatible material of unequal length. FIG. 3B shows the stacked-layers embodiment wherein the expansion loop 110 comprises three layers 111*a*, 111*b*, and 111*c*. In alternative embodiments, the expansion loop 110 may comprise two to six layers. Severing, bioabsorption, or decomposition of the shortest of the layers (i.e., layer 111*c*) expands the expandable surgical implant 100. As is shown in FIG. 3C, at least one layer of biocompatible material should remain in place after the shortest layer is severed.

In the stacked-layer embodiment, each layer 111*a*, 111*b*, 111*c* of the expandable loop 110 is preferably about 2 mm to about 10 mm shorter than the adjacent longer layer in the stack of biocompatible material. In particularly preferred embodiments, each layer of loop 110 is about 5 mm shorter than the immediately overlaying layer of biocompatible material in the stack. Furthermore, the loop 110 is preferably positioned a distance ranging from 3 to 20 mm lateral to the central perpendicular axis 108. In particularly preferred embodiments, the loop 110 closest to the central perpendicular axis 108 is about 6 mm lateral to the central perpendicular axis 108.

Figure 4:
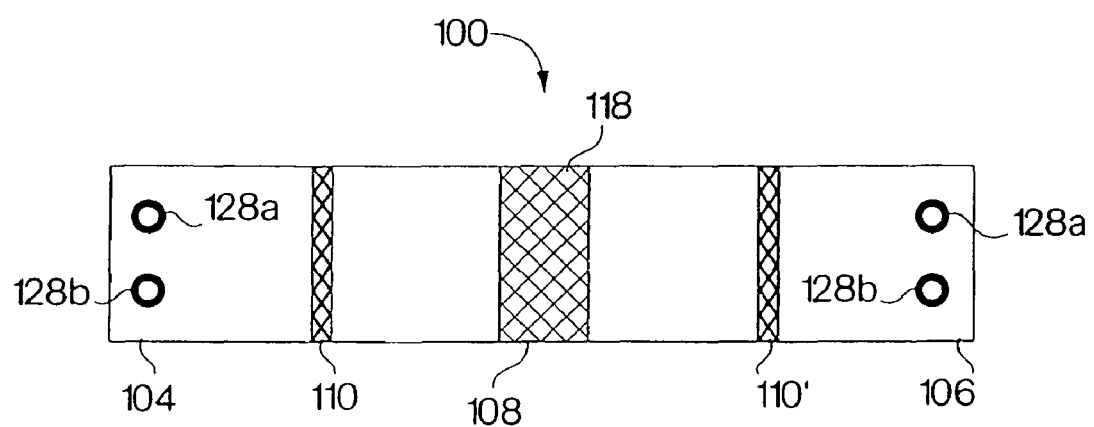
FIG. 4 is a plan view of the embodiment of the expandable implant that includes eyelets positioned near the ends of the surgical implant and a visual indicator positioned in the center of the surgical implant.

FIG. 4 illustrates embodiments in which a visual indicator 118 is disposed along the central perpendicular axis 108 of the expandable surgical implant 100. The visual indicator 118 is a visual guide employed to align the expandable surgical implant 100 with the damaged portion of the patient's body (e.g., the suburethral portion of the implant when the implant is used to treat urinary incontinence). Although the visual indicator 118 is shown in FIG. 1 as a pair of broken lines disposed on either side of the central axis 108 and shown in FIG. 4 as a rectangular strip disposed along the central perpendicular axis 108, it may be otherwise configured and positioned according to the particular application.

When the implant is specifically configured as a sling for treating female urinary stress incontinence, the expansion loop 110 of the stacked layers is preferably positioned away from the central portion (e.g., lateral to the central portions) of the surgical implant and the visual indicator 118 is preferably positioned generally in the central portion of the expandable surgical implant 100 and in the vicinity of the central perpendicular axis 108.

FIG. 4 illustrates an embodiment in which the expandable surgical implant 100 further comprises pairs of reinforced fastener attachment sites 128*a*, 128*b*. These fastener attachments sites may be used to attach a fastener to the expandable surgical implant 100. Fasteners for securing the expandable surgical implant 100 to an anatomical structure of the patient are preferably disposed in the 1 cm region near the ends of the surgical implant 100. The fasteners may be, for example, sutures that are disposed on the expandable surgical implant 100 by threading them through the eyelets 128*a*, and 128*b*. In alternative embodiments, the fastener may comprise a clip, a bone anchor, a staple, and/or other suitable fasteners.

The expandable surgical implant 100 may be made of mammalian tissue(s), synthetic material(s), or a combination of mammalian tissue(s) and synthetic material(s). One or more mammalian tissues including porcine, ovine, bovine, equine, human cadaveric, or tissue-engineered tissue(s) may be employed to make the material. The material may be derived from omni-directional tissue(s) including dermis and/or pericardium. Suitable materials for use in accordance with this invention include a chemically processed acellular human dermis product that preserves, undamaged, the bioactive structural dermal matrix and which is freeze-dried for storage. The removal of cells from the fully intact dermal matrix reduces the risk of rejection and inflammation and provides a basis for soft tissue reconstruction. Such an acellular human dermal matrix is available from Lifecell (Branchburg, N.J.) under the trade designation AlloDerm® acellular tissue.

Alternatively, oriented mammal tissue(s) including rectus fascia and/or fascia lata may be used for the material. Suitable cleaned and sterilized oriented human tissue materials may be obtained from tissue banks. These animal tissues may be dehydrated with a dehydrating fluid, such as ethyl alcohol or the like, prior to treatment with chemical cross-linking agents, to allow for improved penetration. The cross-linking agent cross-links collagen in the tissues to make the tissues stronger and reduce the antigenicity of the tissues. Other agents such as pepsin may also be used to further reduce antigenicity. The tissues may be cross-linked by using one or more of the following treatment agents: glutaraldehyde, dialdehyde, glutaraldehyde starch, dialdehyde starch, an epoxy compound or ionizing radiation. Certain processes (such as heat, radiation or pH change) or agents (such as halogens, enzymes, organic solvents, detergents, sodium hydroxide, hydrochloric acid, sodium hypochlorite or hydrogen peroxide) may be used to inactivate viruses with and without protein coats or to destroy viral agent infectivity during the manufacturing process. The tissue may also be treated with a highly volatile chemical such as, for example, propylene oxide, to assist with the sterilization of the tissue. Sterilization may be accomplished, for example, using one or more of the following treatments: glutaraldehyde, alcohol, propylene oxide or irradiation sterilization. The treatment of the tissue, with a combination of these materials and processes, can both cross-link the tissue and render the tissue sterile for installation inside the body of a patient.

The synthetic material may be a solid material, a weave, a braid, a mesh or an alternate material construction. The synthetic material may be a polymer. Suitable polymer sources include nylon, polyethylene, polyester, polypropylene, fluoropolymers or copolymers thereof. An exemplary synthetic polyester material suitable for use in according to the invention is available under the trade designation Dacron®, from E. I. du Pont de Nemours and Company (Wilmington, Del.). Other suitable synthetic materials include the fluoropolymers polytetrafluoroethylene (PTFE), which has non-melt processible characteristics, and fluorinated ethylene propylene (FEP), which has melt-processible characteristics; both fluoropolymers are available under the trade designation Teflon®, from E. I. du Pont de Nemours and Company (Wilmington, Del.). A suitable PTFE material of solid material construction is a available under the trade designation GORE-TEX®, from W. L. Gore & Associates, Inc. (Flagstaff, Ariz.).

Combinations of synthetic materials and mammalian tissues may also be used according to the invention. These combinations may include material having a combination of parts, including, for example, parts made of synthetic polymers and of processed animal tissues. Such combinations also include materials having both synthetic polymers and animal cells that are treated so as to cross-link the collagen or other commonly antigenic fibers in the animal cells. When a combination of synthetic materials and natural materials is used, it is preferred, but not necessary, that the central portion comprise natural materials and the end portions comprise synthetic materials.

The material is provided in a shape suitable for a medical application, e.g., rectangular, and may include elongated members extending from a central portion of the material. Other suitable shapes may include octagonal, trapezoidal, elliptical and hexagonal shapes. When the surgical implant is specifically configured as sling for use in treating female urinary stress incontinence, the biocompatible material 102 may have a length from about 2.5 cm to about 30 cm in length and a width that ranges from about 1.0 cm to about 3.0 cm.

The expandable surgical implant 100 may be sterilized and packaged in a sterile holder. The packaging conditions may be dry and the package protective of the expandable surgical implant 100 during transport and storage. The packaging may be designed to protect the material of the expandable surgical implant 100 from ultra-violet light to prevent damage. Upon opening the protective package, the implant may be hydrated, if necessary, with, for example, saline solution, and thereafter installed in the patient without any additional alteration by the surgeon performing the surgical procedure.

As will be described in further detail below, the forgoing expandable surgical implants 100 are particularly useful in surgical methods that require minimal invasion (i.e., incision and/or dissection) to expand a surgical implant that has been placed within a body.

In one embodiment, a method of treating a damaged portion of a patient's body employs the expandable surgical implant 100 of the invention. The method includes, in overview, providing the expandable surgical implant 100; positioning the central perpendicular axis 108 axis of implant is so that it lies substantially along a portion of the patient's body to be supported (e.g., the urethra); (optionally) securing the first end 104 of the material of the implant to a first anatomical structure in the body of the patient; applying tensioning force substantially along the longitudinal axis of the material; (optionally) securing the second end 106 of the material to the same or a second anatomical structure in the body of the patient; supporting a damaged portion of the patient's body with the secured material; and expanding one or more expansion loops 110 on the implant to relieve excessive tension.

As described in greater detail above, the expanding step may result from decomposition or severing of a control element or stacked layer. Furthermore, a single expandable surgical implant 100 may comprise multiple expansion loops that may be uncinched separately, using different techniques, providing a physician with the ability to incrementally expand the implant according to the patient's needs.

Figure 5:
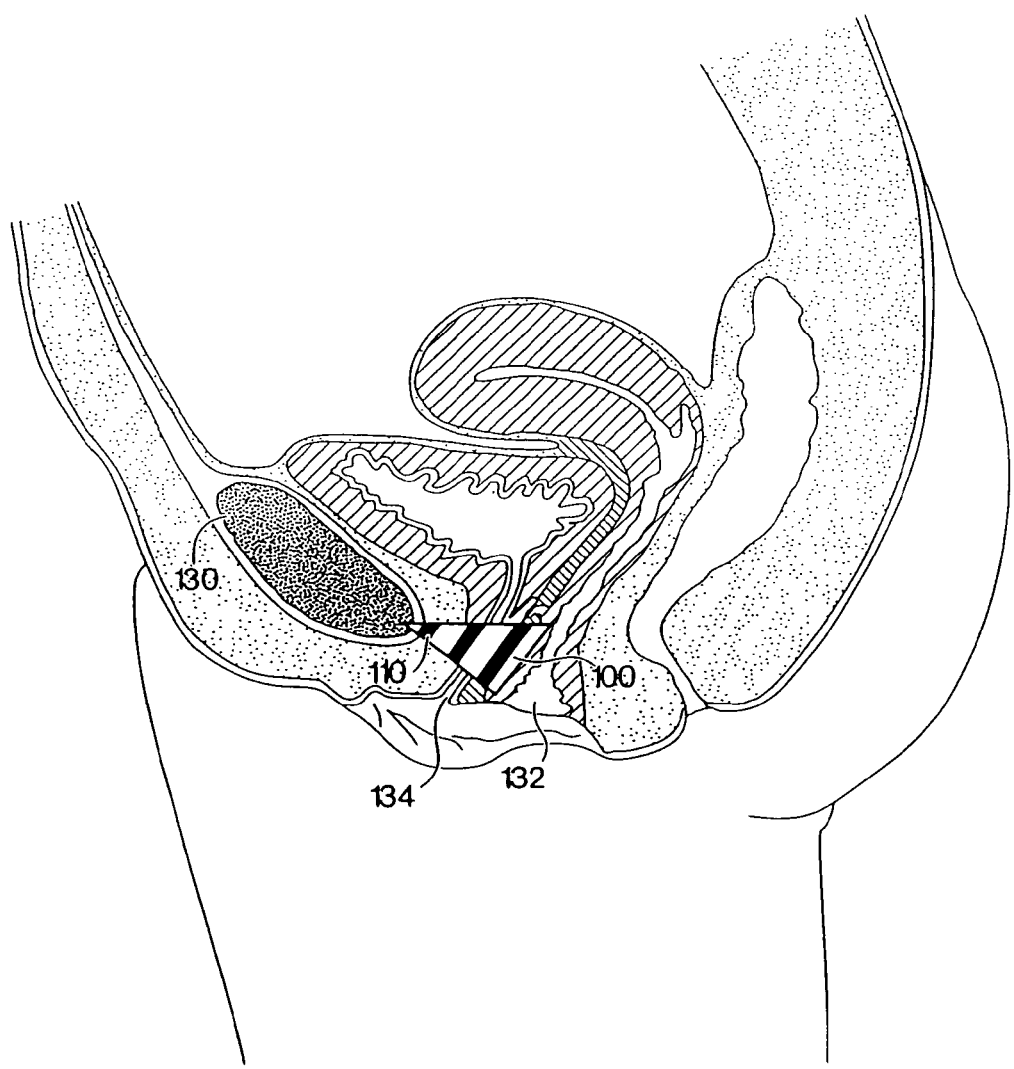
FIG. 5 is a sagittal section of a female pelvis illustrating an expandable surgical implant used in a procedure to treat female urinary incontinence where the implant is anchored to the posterior pubic bone cephalad to the inferior edge.
Figure 6:
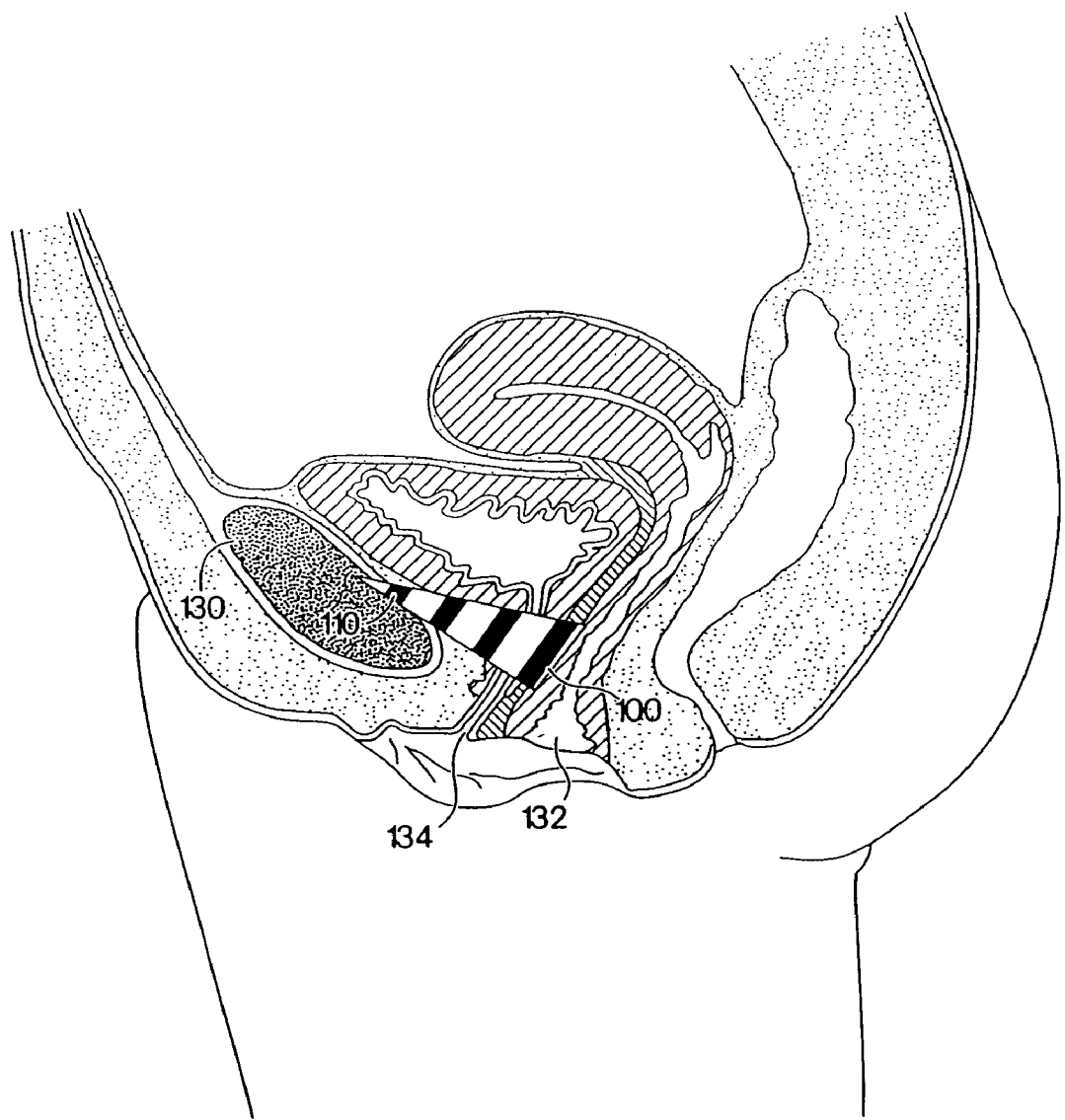
FIG. 6 is a sagittal cross section of a female pelvis illustrating an expandable surgical implant used in a suburethral sling procedure to treat female urinary incontinence where the implant is anchored to the posterior surface of the pubic bone approximately midway between the inferior and superior edges.
Figure 7:
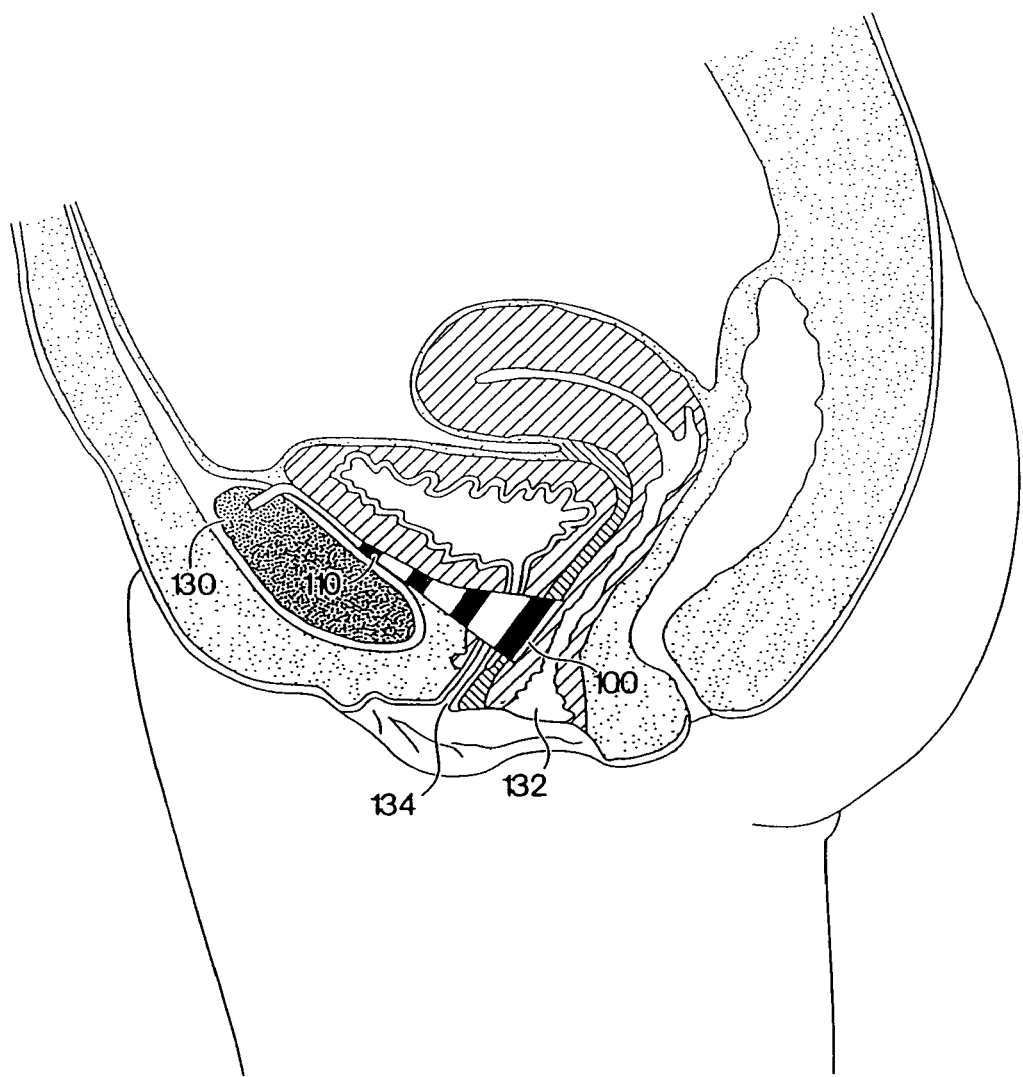
FIG. 7 is a sagittal cross section of a female pelvis illustrating an expandable surgical implant used in a suburethral sling procedure to treat female urinary incontinence where the implant is anchored to the superior surface of the pubic bone.

In one particular embodiment, the expandable surgical implant 100 is employed to treat a female patient suffering from stress urinary incontinence. FIGS. 5-7 show various options available for placement of the medical device of the invention to treat female urinary incontinence. These figures show a sagittal view of a female pelvis including the pubic bone 130, the urethra 134, and the vaginal canal 132. Physiological conditions that cause stress urinary incontinence may include ISD, bladderneck hypermobility, and a combination of the two conditions. When an expandable surgical implant 100 is employed to treat incontinence, it may be used to provide support to the pelvic floor. Where the physiological condition is ISD, the expandable surgical implant 100 may be installed to improve improper coaption of the urethral sphincter. Alternatively, where the condition is hypermobility, the expandable surgical implant 100 may be installed to support, elevate or "back stop" the midurethra. In the patient who suffers from a combination of ISD and hypermobility, an expandable surgical implant 100 may be installed to support one or an of these sites.

In general, approaches to access the body to deliver and install surgical implants for treating female stress incontinence include transvaginal, transabdominal, and combined transvaginal and transabdominal procedures. In some procedures, the expandable surgical implant 100 may be secured to an anatomical structure. A variety of fasteners may be used to secure the implant including bone anchors, staples, bone screws, and/or sutures.

In methods employing a transvaginal approach, an anchor implantation device may be introduced directly through the vaginal wall or, alternatively, through an incision in the anterior vaginal wall. A leading edge of an anchor implantation device may be passed through the anterior vaginal wall to the side of the bladder neck, and a bone anchor may be, optionally, secured to the posterior aspect of the pubic bone (shown in FIGS. 5-7). In other embodiments the implant may be secured to other anatomical structures such as the Cooper's ligament. In alternative embodiments, the implant may be placed within the body without being secured to an anatomical structure. After the implant 100 is position in the body and, optionally, an anchor is driven into the pubic bone, the anchor implantation device is withdrawn and removed leaving the two free ends of suture exiting the endopelvic fascia and trailing the two free ends of the suture from the vaginal wall incision. The above procedure is repeated on the opposite side of the urethra to implant a second anchor.

The expandable surgical implants 100 disclosed herein are designed to be secured to any suitable support structure of a patient's body. Examples of such structures include but are not limited to the bones, ligaments, fascia and appropriate muscle structures proximate to the site of attachment. For example, sutures may be used to attach the implant to the Cooper's ligament or the rectus fascia without using a bone anchor.

In some embodiments, the anchor implant site is located lateral to the symphysis pubis and cephalad to the inferior edge of the pubic bone as shown in FIG. 5. In one particular embodiment, the anchor implant site is located approximately 1 cm lateral to the symphysis pubis and 1 cm cephalad to the inferior edge of the pubic bone. In an alternative embodiment, the expandable surgical implant 100 may be anchored to the posterior surface of the pubic bone mid-way between the inferior and superior surfaces as is shown in FIG. 7. In yet another alternative embodiment, the expandable surgical implant 100 may be anchored the superior surface of the pubic bone as is shown in FIG. 7.

Following installation inside the patient, cells infiltrate the open surface areas of the expandable surgical implant 100 and tissue growth begins. The tissue on both sides of the implant cross communicates such that tissue from both the anterior vaginal wall and urethra grows into the expandable surgical implant 100. This scar tissue growth provides support to the urethra. This tissue growth also secures the implant at the site of installation, thus improving urethra closing pressure and patient continence.

Regardless of the method or the site of implantation, the expandable surgical implant 100 of the invention may be expanded one or more times following implantation. Thus, if the implant was placed too taut or if the patient's anatomy changes due to aging, weight gain, and/or pregnancy the expandable surgical implant 100 of the invention may be expanded to restore a proper tension. For example, the expandable surgical implant 100 of the invention may be expanded post-operatively a first time in the first several weeks following the procedure by severing (e.g., with a scalpel) the expansion loop 110. Subsequently, a second expansion may be accomplished by applying a localized stimulus (ultrasonic waves) to decompose a second expansion loop 10. A third expansion may be accomplished by applying a different localized stimulus (e.g., microwave radiation) to decompose a third expansion loop.

In all embodiments, the expansion loop 110 may be uncinched directly (e.g., mechanically) or indirectly (e.g., using low energy radiation) thereby expanding the implant with minimal invasion. However, in suburethral sling procedures employing embodiments in which the expansion loop 110 is positioned greater than 6 mm lateral to the central perpendicular axis 108, the expansion loops 110 are preferably uncinched indirectly (e.g., using low energy radiation) thereby avoiding the need to dissect tissue to access the expansion loop 110. In embodiments where the expansion loop 110 is positioned 3 to 6 mm lateral to the central perpendicular axis 108 the expansion loop 110 may be uncinched by directly (e.g., mechanically) or indirectly (e.g., using low energy radiation) uncinching the expansion loop with minimal invasion.

In embodiments wherein the control element 114 is radio-opaque, the control element 114 may be visualized using a device such as a fluoroscope to confirm that the control element 114 has been severed and the expansion loop 110 has been uncinched.

Figure 8:
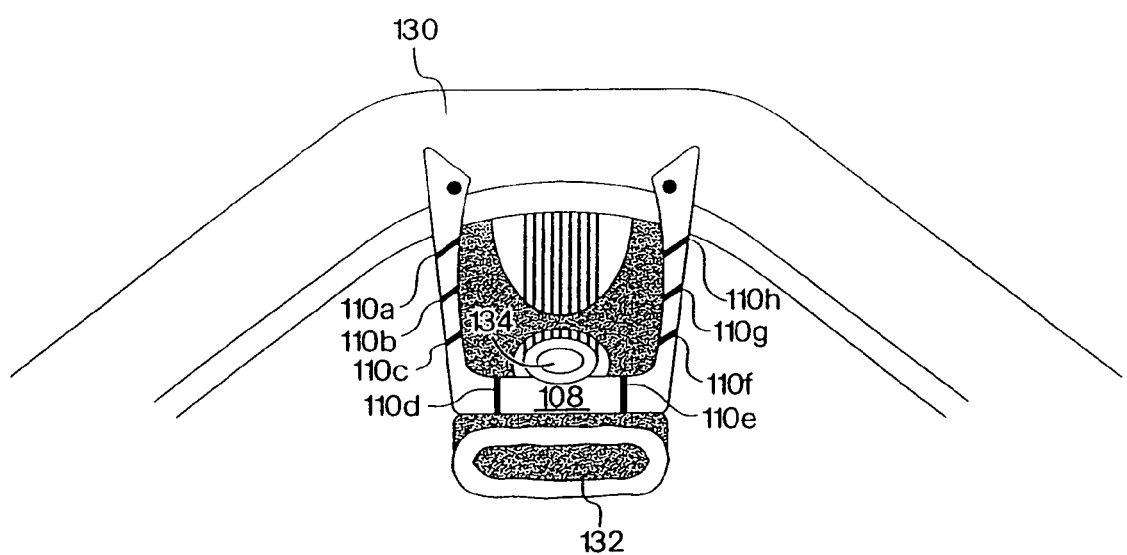
FIG. 8 is a superior view of the pelvic floor of the embodiment shown in FIG. 7.

As is shown in FIG. 8, the expansion loops 110a-110h are preferably positioned away from the central portion 108 of the expandable surgical implant 100 so as to provide maximum suburethral 134 support. As is further shown in FIG. 8, a expandable surgical implant 100 used in suburethral sling procedures preferably comprises and even number of expansion loops thereby permitting the physician to evenly loosen of the expandable surgical implant 100 on both sides lateral to the central perpendicular axis 108 and thereby reduce damage to suburethral tissue that has grown into the central portion of the implant.

Variations, modifications, and other implementations of what is described herein will occur to those of ordinary skill in the art without departing from the spirit and the scope of the invention. Accordingly, the invention is not to be limited only to the preceding illustrative description.

What is claimed is:

1. An expandable surgical implant comprising:
   a biocompatible material having a first end, a second end positioned opposite to the first end, and a central perpendicular axis located substantially equidistant from the first and second ends; and
   at least one expansion loop positioned lateral to the central perpendicular axis, wherein (a) the expansion loop comprises at least one pair of reinforced control element attachment sites positioned on one side of the central perpendicular axis, and at least one control element associated with the attachment sites and drawing the attachment sites into close proximity, wherein the control element extends along substantially all of a width of the biocompatible material, and (b) the expandable loop comprises multiple layers of biocompatible material of unequal length incorporated into the length of biocompatible material.

2. The device of claim 1, comprising 2, 4, or 6 expansion loops positioned lateral to the central perpendicular axis.

3. The device of claim 1, wherein equal number of expansions loops are positioned on opposite sides of the central perpendicular axis.

4. The device of claim 1, wherein a first attachment site is positioned a distance ranging from 3 to 20 mm lateral to the central perpendicular axis.

5. The device of claim 4, wherein a second attachment site is positioned a distance ranging from 3 to 12 mm further from the central perpendicular axis than the first attachment site.

6. The device of claim 4, wherein the second attachment site is positioned a distance of about 5 mm further from the central perpendicular axis than the first control element.

7. The device of claim 1, wherein the layers of biocompatible material are stacked in order of increasing length.

8. The device of claim 1, wherein the layers of biocompatible material are positioned a distance ranging from 3 to 20 mm lateral to the central perpendicular axis.

9. The device of claim 1, wherein the length of biocompatible material comprises synthetic material.

10. The device of claim 1, wherein the length of biocompatible material comprises natural material.

11. The device of claim 1, wherein the length of biocompatible material comprises a combination of natural and synthetic material.

12. The device of claim 11, further comprising a central portion positioned between a first lateral portion and a second lateral portion, wherein the central portion comprises natural material and the lateral portions comprise synthetic material.

13. The device of claim 1, further comprising a visual indicator located along at least a portion of the central perpendicular axis.

14. The device of claim 13, wherein the visual indicator comprises a surgical dye applied along the central perpendicular axis.

15. The device of claim 13, wherein the visual indicator is a radio-opaque material woven into the biocompatible material along the central perpendicular axis.

16. The device of claim 1, wherein the length of biocompatible material is elongate in shape.

17. The device of claim 1, wherein the length of biocompatible material is substantially rectangular in shape.

18. The device of claim 1, wherein the length of biocompatible material is about 20 to 50 cm long with all expansion loops cinched.

* * * * *